US012383283B2

(12) United States Patent
Zuhars et al.

(10) Patent No.: US 12,383,283 B2
(45) Date of Patent: Aug. 12, 2025

(54) TWO DEGREE OF FREEDOM SYSTEM AND METHOD

(71) Applicants: Think Surgical, Inc., Fremont, CA (US); Stan G. Shalayev, Fremont, CA (US)

(72) Inventors: Joel Zuhars, Fremont, CA (US); Stan G. Shalayev, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 355 days.

(21) Appl. No.: 18/073,654

(22) Filed: Dec. 2, 2022

(65) Prior Publication Data

US 2023/0098080 A1 Mar. 30, 2023

Related U.S. Application Data

(63) Continuation of application No. 16/562,841, filed on Sep. 6, 2019, now abandoned, which is a
(Continued)

(51) Int. Cl.
*A61B 17/16* (2006.01)
*A61B 17/17* (2006.01)
(Continued)

(52) U.S. Cl.
CPC ...... *A61B 17/1626* (2013.01); *A61B 17/1757* (2013.01); *A61B 17/7082* (2013.01);
(Continued)

(58) Field of Classification Search
CPC ..... A61B 17/16; A61B 17/1626; A61B 17/17; A61B 17/1757; A61B 17/70;
(Continued)

(56) References Cited

U.S. PATENT DOCUMENTS 8,634,897 B2 1/2014 Simon et al.
2005/0192575 A1 9/2005 Pacheco
(Continued)

FOREIGN PATENT DOCUMENTS

WO 2005081863 A2 9/2005
WO 2014198784 A1 12/2014
(Continued)

OTHER PUBLICATIONS

U.S. Appl. No. 16/562,841, filed Sep. 6, 2019.
(Continued)

*Primary Examiner* — Christopher J Beccia
(74) *Attorney, Agent, or Firm* — MaxGoLaw PLLC

(57) ABSTRACT

A method and system to align a pin or drill a tunnel along a single line in space with a two degree of freedom (2-DOF) surgical device in a patient is provided. A plane is defined relative to a desired location for an implant or tunnel on a bone, where the implant or tunnel has an axis. An end-effector of the 2-DOF surgical device is aligned coincident with the plane, and the 2-DOF surgical device is moved side-to until a first indicator signals when the end-effector aligns with an entry point for the desired location for the implant or tunnel on the bone. A tip of the end-effector is anchored into the bone at the entry point; and the 2-DOF surgical device is rotated about the anchored tip until a second indicator signals when the end-effector aligns with the axis of the implant or tunnel at the desired location.

17 Claims, 11 Drawing Sheets

Related U.S. Application Data continuation-in-part of application No. PCT/US2018/022378, filed on Mar. 14, 2018.

(60) Provisional application No. 62/474,313, filed on Mar. 21, 2017.

(51) Int. Cl.
  *A61B 17/70* (2006.01)
  *A61B 34/10* (2016.01)
  *A61B 90/00* (2016.01)
  *A61B 17/00* (2006.01)
  *A61B 17/68* (2006.01)
  *G16H 20/40* (2018.01)

(52) U.S. Cl.
  CPC .............. *A61B 34/10* (2016.02); *A61B 90/08* (2016.02); *A61B 90/39* (2016.02); *A61B 2017/00128* (2013.01); *A61B 2017/681* (2013.01); *A61B 2034/104* (2016.02); *A61B 2034/105* (2016.02); *A61B 2090/0811* (2016.02); *A61B 2090/3983* (2016.02); *G16H 20/40* (2018.01)

(58) Field of Classification Search
  CPC ..... A61B 17/7082; A61B 34/10; A61B 90/08; A61B 90/39; A61B 90/00
  See application file for complete search history.

(56) References Cited

U.S. PATENT DOCUMENTS

| | | |
|---|---|---|
| 2008/0177203 A1 | 7/2008 | von Jako |
| 2008/0300605 A1 | 12/2008 | Rinner |
| 2015/0100066 A1* | 4/2015 | Kostrzewski ...... A61B 17/1615 606/130 |
| 2016/0354161 A1 | 12/2016 | Deitz |
| 2018/0344409 A1* | 12/2018 | Bonny ................... A61B 34/20 |

FOREIGN PATENT DOCUMENTS

| | | |
|---|---|---|
| WO | WO2016/049180 A1 | 3/2016 |
| WO | 2017091380 A1 | 6/2017 |
| WO | 2018132835 A1 | 7/2018 |
| WO | 2018175172 A1 | 9/2018 |
| WO | 2019173600 A1 | 9/2019 |

OTHER PUBLICATIONS

EP Communication reporting extended search report for EP19205830, dated Aug. 13, 2020.
PCT International Search Report for PCT/2018/022378, dated Jul. 23, 2018, for Think Surgical, Inc.
Supplementary EP Search Report for EP18772376, dated Nov. 26, 2020.
Barsa, et al., "The intraoperative portable CT scanner-based spinal navigation: a viable option for instrumentation in the region of cervico-thoracic junction," European Spine Journal, Springer Verlag, Berlin, DE, vol. 25, No. 6, Mar. 17, 2016 (Mar. 17, 2016), pp. 1643-1650.
Shunsuke, et al., "Strategy for salvage pedicle screw placement: A technical note," The International Journal of Spine Surgery, vol. 7, No. 1, Jan. 1, 2013 (Jan. 1, 2013), pp. e67-e71.
Bodon, et al., "Applied anatomy of screw placement via the posterior arch of the atlas and anatomy-based refinements of the technique," European Journal of Orthopaedic Surgery & Traumatology, Springer Paris, Paris, vol. 26, No. 7, Apr. 22, 2016 (Apr. 22, 2016), pp. 793-803.

* cited by examiner

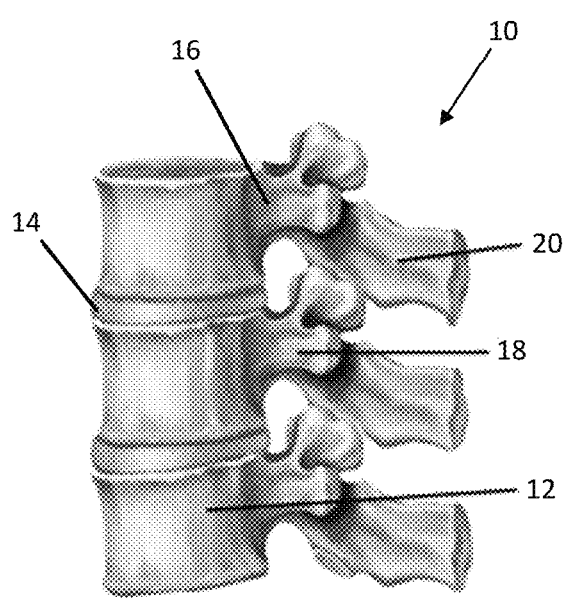
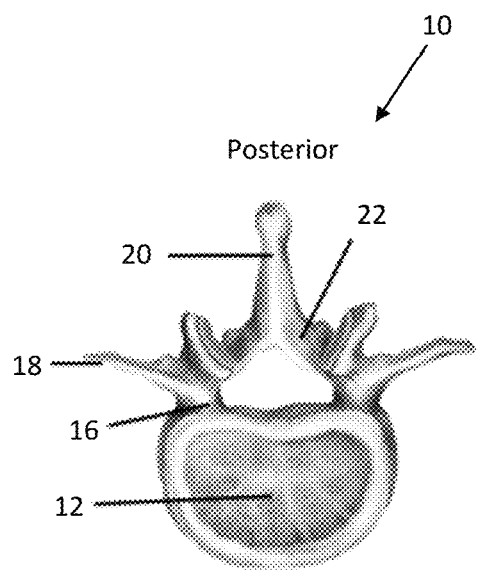
FIG. 1A
(Prior art)
FIG. 1B
(Prior art)
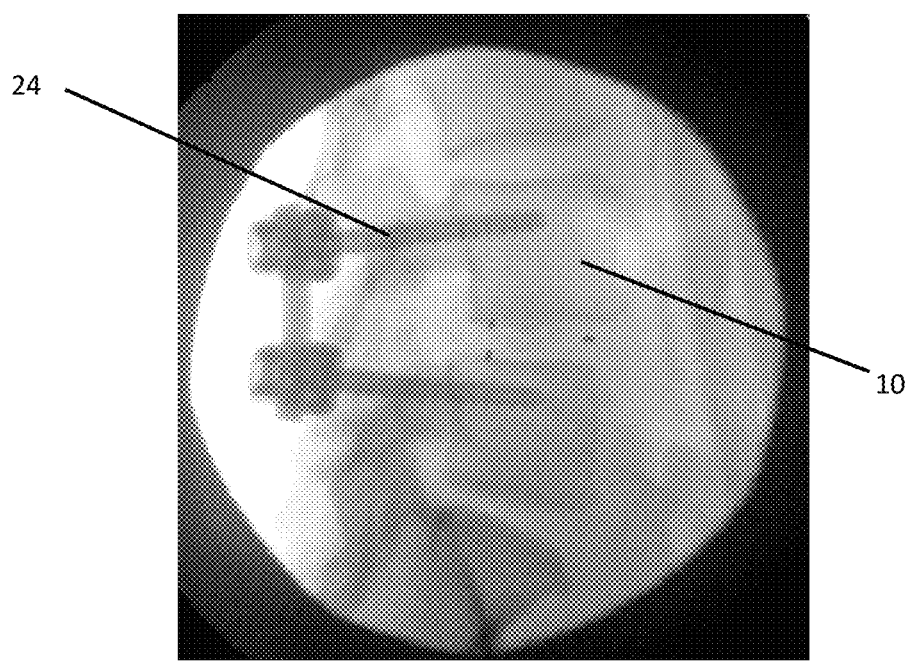
FIG. 2
(Prior art)

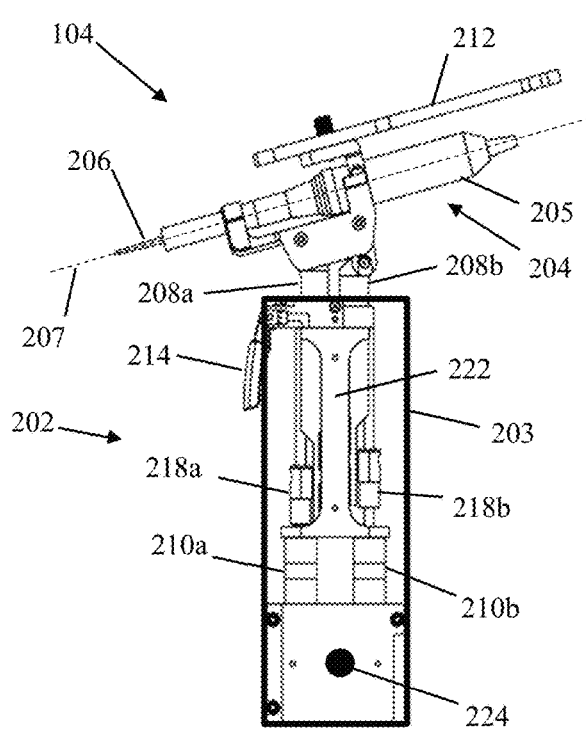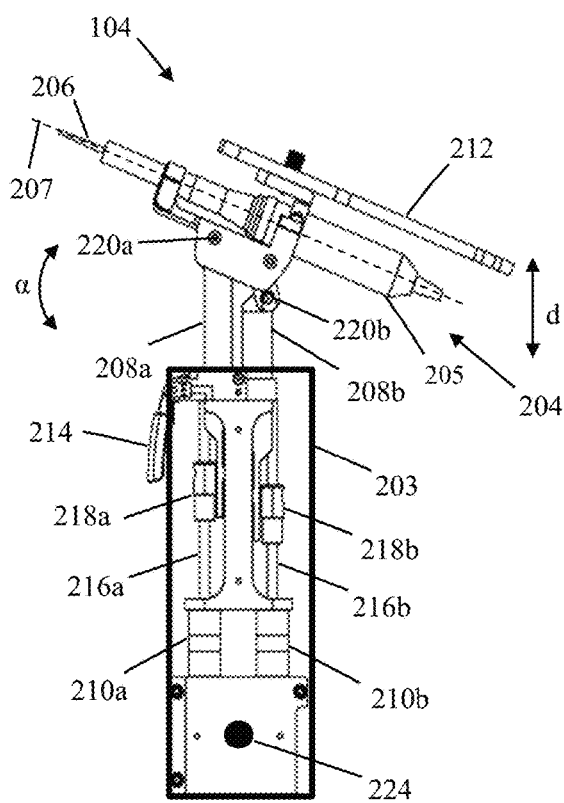
FIG. 4A
FIG. 4B

TWO DEGREE OF FREEDOM SYSTEM AND METHOD

RELATED APPLICATIONS

This application is a continuation of U.S. Utility application Ser. No. 16/562,841, filed 6 Sep. 2019, that is a continuation-in-part of PCT Application Number PCT/US2018/022378, filed 14 Mar. 2018, that in turn claims priority benefit of U.S. Provisional Application Ser. No. 62/474,313, filed 21 Mar. 2017, the contents of which are hereby incorporated by reference.

FIELD OF THE INVENTION

The present invention generally relates to computer assisted surgery, and more specifically to systems and methods for aligning a two degree of freedom device along a line representative of an optimal and planned trajectory and for aligning and inserting a pedicle screw through the pedicle in a desired position and orientation based on a preoperative planned optimal trajectory.

BACKGROUND

A two degree of freedom (2-DOF) Surgical System is well suited for aligning pins on a plane or cutting along a plane. However, the 2-DOF surgical system lacks degrees of freedom to align a pin (or drill a tunnel) along a single line in space. Having the ability to align the 2-DOF surgical system on a line is particularly advantageous for drilling bone tunnels (e.g., ACL reconstruction) or inserting screws into a bone (e.g., pedicle screws for spine). In currently pending PCT application PCT/US2018/022378 filed 14 Mar. 2018 that is included herein in its entirety, the use of a 2-DOF system for inserting pedicle screws into a pedicle (essentially aligning the 2-DOF on a line). The remaining degrees of freedom were accounted for in that application using visual feedback from a monitor and blinking light emitting diodes (LEDs) on the device.

The vertebral column, also known as the backbone or spinal column, is part of the axial skeleton. The vertebral column is made up of a segmented series of bones called vertebrae that are separated by intervertebral discs. The vertebral column houses the spinal canal, a cavity that encloses and protects the spinal cord. In the human vertebral column, there are normally thirty-three vertebrae; the upper twenty-four are articulating and separated from each other by intervertebral discs, and the lower nine are fused in adults, five in the sacrum and four in the coccyx or tailbone. The articulating vertebrae are named according to their region of the spine. There are seven cervical vertebrae, twelve thoracic vertebrae and five lumbar vertebrae. The pedicle is a narrow piece of bone in the form of a dense stem-like structure that projects from the posterior of a vertebra. There are two pedicles per vertebra. A series of pedicles traverse the spinal column and join the transverse process with the vertebral body.

FIGS. 1A and 1B illustrate a segment and a cross sectional view, respectively of a spinal column 10. As shown the spinal column 10 has a series of vertebrae 12 separated from each by intervertebral discs 14. The pedicles 16 extend from the vertebrae 12 and join the transverse process 18 to the vertebrae 12. The spinous process 20 extends from the lamina 22, which are connected to the opposing sides of the transvers process 18.

A pedicle screw is a particular type of bone screw designed for implantation into a vertebral pedicle. Pedicle screws are used to correct deformity, and/or treat trauma inflicted to a patient spinal column. Pedicle screws may be used in instrumentation procedures to affix rods and plates to the spine. The screws may also be used to immobilize part of the spine to assist in decompression of neural elements (spinal cord, exiting nerve roots, cauda equine contained nerve tracks) and fusion by holding bony structures together. FIG. 2 is an X-ray image of pedicle screws 24 inserted in a spinal column 10 of patient.

Currently, there are several navigation systems available that provide visual feedback to aid in the alignment of pedicle screws through the pedicle. However, trying to align the pedicle in 5-DOF through this narrow piece of bone is often difficult and time consuming when only relying on visual feedback. The procedure becomes even more difficult in the upper thoracic and cervical regions of the spine as the vertebral pedicles progressively narrow.

The position and orientation (POSE) of the inserted pedicle screws into a vertebra is highly critical to a safe and successful outcome. Generally, surgeons plan and create an implantation plan so the final placement of the implanted screws provides the necessary support or immobilization to the section of the patient spinal column. Even small implant alignment deviations outside of clinically acceptable ranges correlates to less than optimal outcomes and increased rates of follow up surgery.

While improved systems and methods for aligning and inserting a pedicle screw through the pedicle in a desired position and orientation based on a preoperative planned optimal trajectory have been made, there continues to be a need for system enhancements and an improved method of using a 2-DOF system to align a pin (or drill a tunnel) along a single line in space.

SUMMARY

A method is provided herein to align a 2-DOF hand-held surgical device along an axis. The method includes defining a plane relative to a desired location for an implant or tunnel on a bone, where the implant or tunnel has an axis. An end-effector of the 2-DOF surgical device is aligned coincident with the plane, and the 2-DOF surgical device is moved side-to-side while the end-effector maintains coincidence with the plane until a first indicator signals when the end-effector aligns with an entry point for the desired location for the implant or tunnel on the bone. Subsequently, a tip of the end-effector is anchored into the bone at the entry point; and the 2-DOF surgical device is rotated about the anchored tip while the end-effector remains coincident with the plane until a second indicator signals when the end-effector aligns with the axis of the implant or tunnel at the desired location. The end-effector is then inserted into the bone.

A system for implementing the method to align a 2-DOF hand-held surgical device along an axis includes a computing system, an articulating 2-DOF surgical device, and a tracking system.

BRIEF DESCRIPTION OF THE DRAWINGS

The present invention is further detailed with respect to the following drawings. These figures are not intended to limit the scope of the present invention but rather illustrate certain attributes thereof wherein;

FIGS. 1A and 1B illustrate a segment and a cross sectional view, respectively of a spinal column;

FIG. 2 in a prior art X-ray image of pedicle screws inserted in a patient's spinal column

FIGS. 4A and 4B depict a surgical device used in the surgical system;

FIG. 6A depicts the device having a pin/screw in a retracted state, and FIG. 6B depicts the device having a pin/screw in an extended state in accordance with embodiments of the invention;

DETAILED DESCRIPTION OF THE INVENTION

Figure 3A:
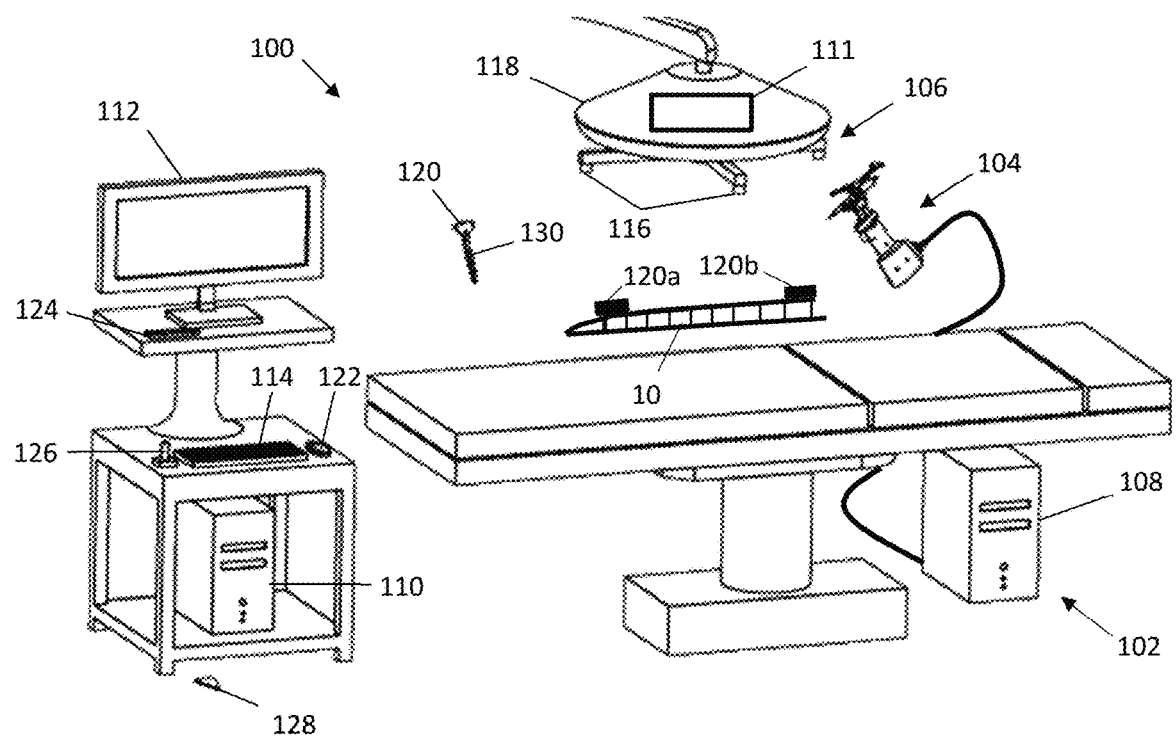
FIGS. 3A and 3B depict a surgical system to perform a procedure for implanting pedicle screws in a patient spinal column and with respect to a knee surgical procedure, in accordance with embodiments of the invention.

The present invention has utility as a method and system to aid a surgeon in efficiently and precisely positioning a pedicle screw through the pedicle of a patient spinal column, and an improved method of using a 2-DOF system to align an end-effector of a 2-DOF surgical device along a single line in space.

Embodiments of the inventive method and system in some embodiments, utilize a two degree of freedom (2-DOF) device to aid a surgeon in aligning and inserting a pedicle screw through a targeted pedicle in a desired position and orientation while aligning with a preoperative planned optimal trajectory. Embodiments of the inventive method and system for pedicle screw placement may use visual feedback or other mechanisms to provide alignment in the remaining relevant degrees-of-freedom. Use of a handheld actuator in specific embodiments helps to avoid the possibility of inaccuracy in critical directions due to unintended mechanical deflection of a drill guide when a drill is used through the handheld actuator, such as when a robot is used to hold the drill guide.

The method and system are especially advantageous for spinal fusion, and to correct deformity, and/or treat trauma to the spinal column, however, it should be appreciated that other medical applications may exploit the subject matter disclosed herein such as high tibial osteotomies, spinal reconstruction surgery, and other procedures requiring the precise placement for screw implantation.

The following description of various embodiments of the invention is not intended to limit the invention to these specific embodiments, but rather to enable any person skilled in the art to make and use this invention through exemplary aspects thereof.

In embodiments of the inventive method, images of the patient spinal column are acquired. These images are readily collected pre-operatively or intra-operatively with a computer tomography scanner, magnetic resonance imaging scanner, fluoroscopy, ultrasound, or other intracorporal interrogation scanning technique. Two-dimensional orthogonal planar images or a generated 3-D model of the spinal column is then generated and used to define a pedicle plane on a pedicle of the spinal column for each of the pedicle screws to be implanted. A trajectory for each of the pedicle screw to be implanted along the pedicle plane is then determined. In a specific inventive embodiment, the pedicle plane is defined through the center of the pedicle in the medial-lateral direction and in internal-external rotation. This ensures that the 2-DOF device accounts for the narrowest region of the pedicle (medial-lateral distance). A monitor, or an on-board indicator on an embodiment of a 2-DOF surgical tool, can provide simultaneous feedback to allow the user, in real time, to align the pedicle screw in a superior-inferior translation, an anterior-posterior translation (depth), and a flexion-extension angle (angle of rotation in the sagittal plane). It should be noted that intra-operative registration of the patient anatomy relative to any pre-operative images and a reference marker (e.g., radiopaque marker, fiducial marker, fiducial marker array, mechanically tracked probe, or a combination thereof) on the patient anatomy is performed by traditional means, illustratively including two dimensional/three dimensional (2D/3D) fluoro, structured light, or surface point registration. The 2-DOF device may then locate the pedicle plane correctly relative to the anatomy, and also can adjust the device position in real-time to accommodate minor patient motion, such as from breathing or cardiac output.

In terms of planning, a user may locate three medial-lateral (M-L) center points on the pedicle to define the pedicle plane. The user may then plan the remaining DOFs accordingly, or use real-time visual progressive feedback like traditional navigation systems for the remaining DOFs.

Embodiments of the 2-DOF device used in inventive embodiments may be configured to both drill a pilot hole for a pedicle screw, and subsequently drive the pedicle screw into the pedicle. An on-board indicator on the 2-DOF device, illustratively including a light emitting diode (LED), may provide the user with direct visual feedback when the device is aligned in an optimal trajectory and depth perception for the sequential screw advancement and positioning is achieved. Other on-board mechanisms may illustratively include blinking arrows or the like, can help the user align the remaining degrees of freedom in real time.

One or more LED indicators, either on an embodiment of the 2-DOF device or in the user's line of sight, can provide further feedback during pedicle screw advancement to aid in aligning and/or verifying the screw's optimal position. For example, in a specific embodiment a first green light is used to indicate that the entrance point and trajectory of the pedicle screw is correct; a second green light may indicate that mid portion of the pedicle is within a safety zone and the trajectory is confirmed to be correct; a third green light indicates that an end point into vertebral body has been reached and the trajectory of the placement of the pedicle screw is confirmed. When all three LED lights and LED arrows are lit placement of the pedicle screw is completed successfully. In a specific embodiment, left (L) and right (R) three dimensional arrows may be used as trajectory guides, potentially utilizing additional tracking mechanisms illustratively including inertial measuring units (IMUs), accelerometers, and gyroscopes.

Embodiments of the present invention may be implemented with a surgical system. Examples of surgical systems used in embodiments of the invention illustratively include a 1-6 degree of freedom hand-held surgical system, a serial-chain manipulator system, a parallel robotic system, or a master-slave robotic system, as described in U.S. Pat. Nos. 5,086,401, 7,206,626, 8,876,830 and 8,961,536, U.S. Patent Publication No. 2013/0060278. In a specific embodiment, the surgical system is a serial-chain manipulator system as described in U.S. Pat. No. 6,033,415 assigned to the assignee of the present application and incorporated by reference herein in its entirety. The manipulator system may provide autonomous, semi-autonomous, or haptic control and any combinations thereof. In a specific embodiment, a tool attached to the manipulator system may be manually maneuvered by a user while the system provides at least one of power, active or haptic control to the tool.

Figure 3B:
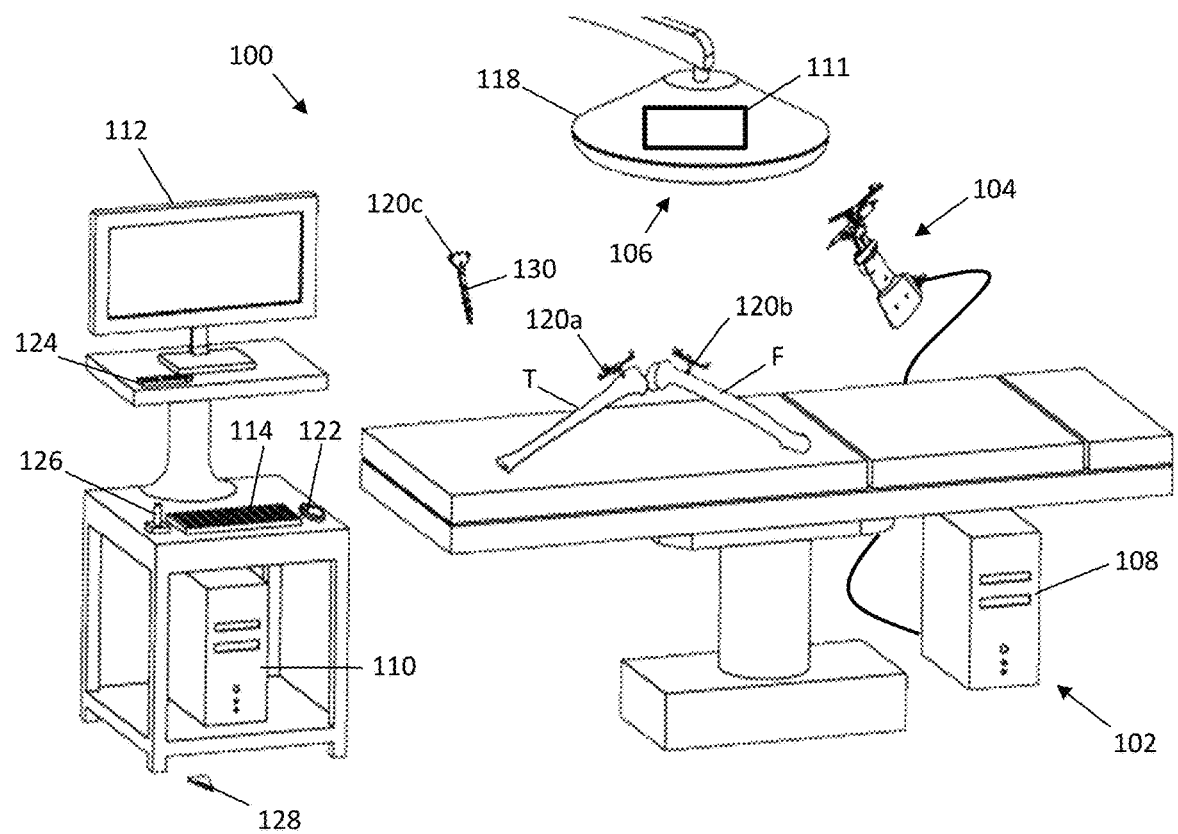

With reference to the figures, FIGS. 3A and 3B illustrate a 2-degree-of-freedom (2-DOF) surgical system 100. The 2-DOF surgical system 100 is generally described in U.S. Patent Publication No. 2015/051713, assigned to the assignee of the present application and incorporated by reference herein in its entirety. The 2-DOF surgical system 100 includes a computing system 102, an articulating surgical device 104, and a tracking system 106. The surgical system 100 is able to guide and assist a user in accurately placing pedicle screws coincident with a virtual pedicle plane that is defined relative to a targeted pedicle bone on a patient's spinal column as shown in FIG. 3A, and in a tibia or fibula in FIG. 3B. It is appreciated that other surgical procedures may be conducted with the surgical system 100. The virtual plane is defined in a surgical plan such that a pedicle screw is inserted in a planned position and orientation.

Articulating Surgical Device

FIGS. 4A and 4B illustrate the articulating surgical device 104 of the 2-DOF surgical system 100 in more detail, where FIG. 4A illustrates the surgical device 104 in a first working POSE and FIG. 4B illustrates the surgical device 104 in a second working POSE. The surgical device 104 includes a hand-held portion 202 and a working portion 204. The hand-held portion 202 includes an outer casing 203 of ergonomic design to be held, wielded, and manipulated by a user. The working portion 204 includes an end-effector/tool 206 having an axis 207. The tool 206 is readily attached to and driven by a motor 205. The hand-held portion 202 and working portion 204 are connected by a front linear rail 208a and a back linear rail 208b that are actuated by components in the hand-held portion 202 to control the pitch and translation of the working portion 204 relative to the hand-held portion 202. A tracking array 212, having three or more fiducial markers, is rigidly attached to the working portion 142 to permit a tracking system 106 to track the POSE of the working portion 204. The three or more fiducial markers may alternatively be integrated directly onto the working portion 204. The fiducial markers may be active markers such as light emitting diodes (LEDs), or passive markers such as retroreflective spheres. The device 104 may further include one or more user input mechanisms such as a trigger 214 or a button.

Within the outer casing of the hand-held portion 202 are a front actuator 210a that powers a front ball screw 216a and a back actuator 210b that powers a back ball screw 216b. The actuators (210a, 210b) may be servo-motors that bi-directionally rotate the ball screws (216a, 216b). A first end of the linear rails (208a, 208b) are attached to the working portion 204 via hinges (220a, 220b), where the hinges (220a, 220b) allow the working portion 204 to pivot relative to the linear rails (208a, 208b). Ball nuts (218a, 218b) are attached at a second end of the linear rails (208a, 208b). The ball nuts (218a, 218b) are in mechanical communication with the ball screws (216a, 216b). The actuators (210a, 210b) power the ball screws (216a, 216b) which cause the ball nuts (218a, 218b) to translate along the axis of the ball screws (216a, 216b). Accordingly, the translation 'd' and pitch 'α' of the working portion 204 may be adjusted depending on the position of each ball nut (218a, 218b) on their corresponding ball screw (216a, 216b). A linear guide 222 may further constrain and guide the motion of the linear rails (208a, 208b) in the translational direction 'd'.

An input/output port in some inventive embodiments of the articulating surgical device 104 provides power and/or control signals to the device 104; or the device may receive power from batteries and control signals via a wireless connection alleviating the need for electrical wiring to be connected to the device 104. The actuators 210 and motor 205 of the articulating surgical device 104 may be controlled using a variety of methods. In one method, control signals may be provided via an electrical connection to an input/output port. In another method, control signals are communicated to the device 104 via a wireless connection alleviating the need for electrical wiring. The wireless connection may be made via optical communication. In a third method, the hand-held portion 202 may house a device computer (or microcontroller) to provide on-board control to the surgical device 104. The on-board device computer may receive external data (e.g., tracking data, informational data, workflow data, etc.) via optical communication. Likewise, the on-board device computer may send internal data (e.g., operational data, actuator/ball-screw position data, battery life, etc.) via optical communication. In a particular embodiment, the device may receive wireless control signals via visible light communication as described in PCT publication WO 2016/081931 and incorporated by reference herein in its entirety.

The articulating surgical device 104 may further include one or more indicators 224 visible to the user. The one or more indicators 224 may be a light emitting diode (LED) or other visual indicator to provide signals to the user, such as the signals to notify the user when the position of the end-effector 206 is aligned with an entry point or axis of the desired location of the implant or tunnel. In specific embodiments, a control system controlling the hand-held surgical device 104 contains software that when executed by one or more processors causes the processor(s) to signal to the user when the end-effector 206 is aligned with an entry-point or axis of a desired location of an implant or tunnel by way of the one or more indicators 224. The one or more indicators 224 may further provide information about the surgical device (e.g., battery life, operating conditions).

Computing System and Tracking System

FIGS. 3A and 3B also detail the computing system 102 that generally includes hardware and software for executing a surgical procedure. In particular inventive embodiments, the computing system 102 provides actuation commands to the actuators (210a, 210b) to control the position and orientation (POSE) of the end effector/tool 206. The computing system 102 is configured to maintain the end-effector 206 coincident with a defined plane independent of the POSE of the hand-held portion 202. The computing system 102 accurately maintains the end-effector/tool 206 coincident with the plane based on: a) the tracked POSE of the plane defined or registered to the bone; and b) the tracked POSE of the working portion 204. The computing system 102 can thus maintain the tool axis 207 with a virtual plane defined in a surgical plan independent of the POSE of the hand-held portion 202.

The computing system 102 in some inventive embodiments may include: a device computer (or microcontroller) 108 including a processor; a planning computer (or microcontroller) 110 including a processor; a tracking computer (or microcontroller) 111 including a processor, and peripheral devices. Processors operate in the computing system 102 to perform computations associated with the inventive system and method. It is appreciated that processor functions are shared between computers, a remote server, a cloud computing facility, or combinations thereof.

The data gathered by and/or the operations performed by the tracking computer 111 and the device computer 108 may work together to control the hand-held surgical device 104 and as such, the data gathered by and/or the operations performed by the tracking computer 111 and device computer 108 to control the surgical device 104 may be referred to herein as a "control system". However, it should be appreciated that the device computer 108, the planning computer 110, and the tracking computer 111 may be separate entities as shown, or it is contemplated that operations may be executed on one or two computers depending on the configuration of the surgical system 100. For example, the tracking computer 111 may have operational data to control the surgical device 104 without the need for a device computer 108. Or, the device computer 108 may include operational data to plan to the surgical procedure without the need for the planning computer 110. Further, any combination of the device computer 108, planning computer 110, and/or tracking computer 111 may be connected via a wired or wireless connection.

In particular inventive embodiments, the device computer 108 may include one or more processors, controllers, software, data, utilities, and any additional data storage medium such as RAM, ROM or other non-volatile or volatile memory to perform functions related to the operation of the surgical device 104. For example, the device computer 108 may include software, data, and utilities to control the surgical device 104 such as the POSE of the working portion 204, receive and process tracking data, control the speed of the motor 205, execute registration algorithms, execute calibration routines, provide workflow instructions to the user throughout a surgical procedure, as well as any other suitable software, data or utilities required to successfully perform the procedure in accordance with embodiments of the invention.

The device computer 108, the planning computer 110, and the tracking computer 111 may be separate entities as shown, or it is contemplated that their operations may be executed on just one or two computers depending on the configuration of the surgical system 100. For example, the tracking computer 111 may have operational data to control the device 104 without the need for a device computer 108. Or, the device computer 108 may include operational data to plan to the surgical procedure with the need for the planning computer 110. In a specific inventive embodiment, the device computer 108 may be located separate from the surgical device 104 as shown in FIGS. 3A and 3B, or the device computer 108 may be housed in the hand-held portion 202 of the surgical device 104 to provide on-board control based on information and/or tracking data received from the tracking computer 111.

Peripheral devices allow a user to interface with the surgical system 100 and may include: one or more user interfaces, such as a display or monitor 112 that may be used to display a graphical user interface (GUI); and various user input mechanisms, illustratively including a keyboard 114, mouse 122, pendent 124, joystick 126, foot pedal 128, or the monitor 112 may have touchscreen capabilities. In addition, the articulating surgical device 104 may have one or more input mechanisms illustratively including buttons and switches, etc.

The planning computer 110 is preferably dedicated to planning the procedure either pre-operatively or intra-operatively. For example, the planning computer 110 may contain hardware (e.g., processors, controllers, and memory), software, data, and utilities capable of receiving and reading medical imaging data, segmenting imaging data, constructing and manipulating three-dimensional (3D) virtual models, storing and providing computer-aided design (CAD) files such as bone pin CAD files, planning the POSE of bone tunnels and/or 3-D virtual implants relative to the bone, pedicle screw CAD files, planning the POSE of implants and/or pedicle screws relative to the bone, providing analysis of region of interest (ROI) pedicle bone density and utilization of ROI information to define interface and maximize screw pitch/bone structural elements integration, generating the surgical plan data for use with the system 100, and providing other various functions to aid a user in planning the surgical procedure. The planning computer also contains software dedicated to defining virtual planes with regards to embodiments of the invention as further described below. The final surgical plan data may include an image data set of the bone, bone registration data, subject identification information, the POSE of one or more pedicle screws relative to the bone, the POSE of one or more virtual planes defined relative to the bone, and any tissue modification instructions. The device computer 108 and the planning computer 110 may be directly connected in the operating room, or may exist as separate entities. The final surgical plan is readily transferred to the device computer 108 and/or tracking computer 111 through a wired or wireless connection in the operating room (OR); or transferred via a non-transient data storage medium (e.g., a compact disc (CD), a portable universal serial bus (USB drive)) if the planning computer 110 is located outside the OR. As described above, the computing system 102 may act as a single entity, with multiple processors, capable of performing the functions of the device computer 108, the tracking computer 111, and the planning computer 110, or any combination thereof. Wireless connections for transfer of information and control may include the use of optical signals or radio waves.

The computing system 102 may accurately maintain the tool axis 207 in 3-D space based on POSE data from the tracking system 106 as shown in FIG. 3. The tracking system 106 generally includes a detection device to determine the POSE of an object relative to the position of the detection device. In a particular inventive embodiment, the tracking system 106 is an optical tracking system as described in U.S. Pat. No. 6,061,644, having two or more optical receivers 116 to detect the position of fiducial markers arranged on rigid bodies. Illustrative examples of the fiducial markers include: an active transmitter, such as an LED or electromagnetic radiation emitter; a passive reflector, such as a plastic sphere with a retro-reflective film; or a distinct pattern or sequence of shapes, lines or other characters. A set of fiducial markers arranged on a rigid body is referred to herein as a fiducial marker array (120a, 120b, 120c, 212), where each fiducial marker array (120a, 120b, 120c, 212) has a unique geometry/arrangement of fiducial markers, or a unique transmitting wavelength/frequency if the markers are active LEDS, such that the tracking system 106 can distinguish between each of the tracked objects. In a specific embodiment, the fiducial marker arrays (120a, 120b, 120c, 212) include three or more active emitters or passive reflectors uniquely arranged in a known geometry on each rigid body. In another embodiment, the fiducial marker array attached to the patient (120a, 120b) may include fiducial markers and radiopaque markers uniquely arranged in a known configuration on a rigid body so as to permit image registration with fluoro or CT and subsequently track the bone with an optical tracking system.

The tracking system 106 may be built into a surgical light 118, located on a boom, stand, or built into the walls or ceilings of the operating room. The tracking system computer 111 includes tracking hardware, software, data, and utilities to determine the POSE of objects (e.g., bones such as the spinal column 10, the femur F and tibia T, the surgical device 104) in a local or global coordinate frame. The output from the tracking system 106 (i.e., the POSE of the objects in 3-D space) is referred to herein as tracking data, where this POSE data is readily communicated to the device computer 108 through a wired or wireless connection. Alternatively, the device computer 108 may determine the POSE data using the position of the fiducial markers detected directly from the optical receivers 116.

The tracking or POSE data is determined using the position of the fiducial markers detected from the optical receiver/detectors 116 and operations/processes such as image processing, image filtering, triangulation algorithms, geometric relationship processing, registration algorithms, calibration algorithms, and coordinate transformation processing.

POSE data from the tracking system 106 is used by the computing system 102 to perform various functions. For example, the POSE of a digitizer probe 130 with an attached probe fiducial marker array 120c may be calibrated such that tip of the probe is continuously known as described in U.S. Pat. No. 7,043,961. The POSE of the tip or axis of the tool 206 may be known with respect to the device fiducial marker array 212 using a calibration method as described in PCT Publication WO 2016/141378. Registration algorithms are readily executed using the POSE data to determine the POSE and/or coordinate transforms between a bone, a surgical plan, and a surgical system. For example, in registration methods as described in U.S. Pat. Nos. 6,033,415 and 8,287,522, points on a patient's bone may be collected using a tracked digitizer probe to transform the coordinates of a surgical plan, coordinates of the bone, and the coordinates of a surgical device. The bone may also be registered using image registration as described in U.S. Pat. No. 5,951,475. The coordinate transformations may be continuously updated using the POSE data from a tracking system tracking the POSE of the bone post-registration and the surgical device.

It should be appreciated that in certain inventive embodiments, other tracking systems are incorporated with the surgical system 100 such as an electromagnetic field tracking system, ultrasound tracking systems, accelerometers and gyroscopes, or a mechanical tracking system. The replacement of a non-mechanical tracking system with other tracking systems should be apparent to one skilled in the art. In specific embodiments, the use of a mechanical tracking system may be advantageous depending on the type of surgical system used such as the one described in U.S. Pat. No. 6,322,567 assigned to the assignee of the present application and incorporated by reference in its entirety.

In the surgical system 100, an optical tracking system 106 with optical receivers 116 is used to collect POSE data of the spinal column. Tracking arrays 120a and 120b are attached to the spinal column 10 where subsequently one or more target vertebral bodies are registered to a surgical plan. In a specific embodiment, the tracking arrays 120a and 120b are screwed into the spinous process 20. The POSE of the spinal column is tracked in real-time by the tracking system 106 so the coordinate transformation between the surgical plan and the surgical device are updated as the bones and surgical device move in the operating space. Therefore, a relationship between the POSE of the tool 206 and the POSE of any coordinates defined in the surgical plan may be determined by the computing system 102. In turn, the computing system 102 can supply actuation commands to the actuators (210a, 210b) in real-time to accurately maintain the tool axis 207 to the defined coordinates.

Additionally, user input mechanisms, such as the trigger 214 or foot pedal 128, may be used by the user to indicate to the computing system 102 that the tool axis 207 needs to be maintained to other coordinates defined in a surgical plan. For example, the tool axis 207 may be maintained in a first defined plane, and the user may step on the foot pedal 128 to relay to the computing system 102 that the tool axis 207 needs to be maintained in a second defined plane.

Surgical Planning and Execution for a Spinal Surgical Application

Figure 5:
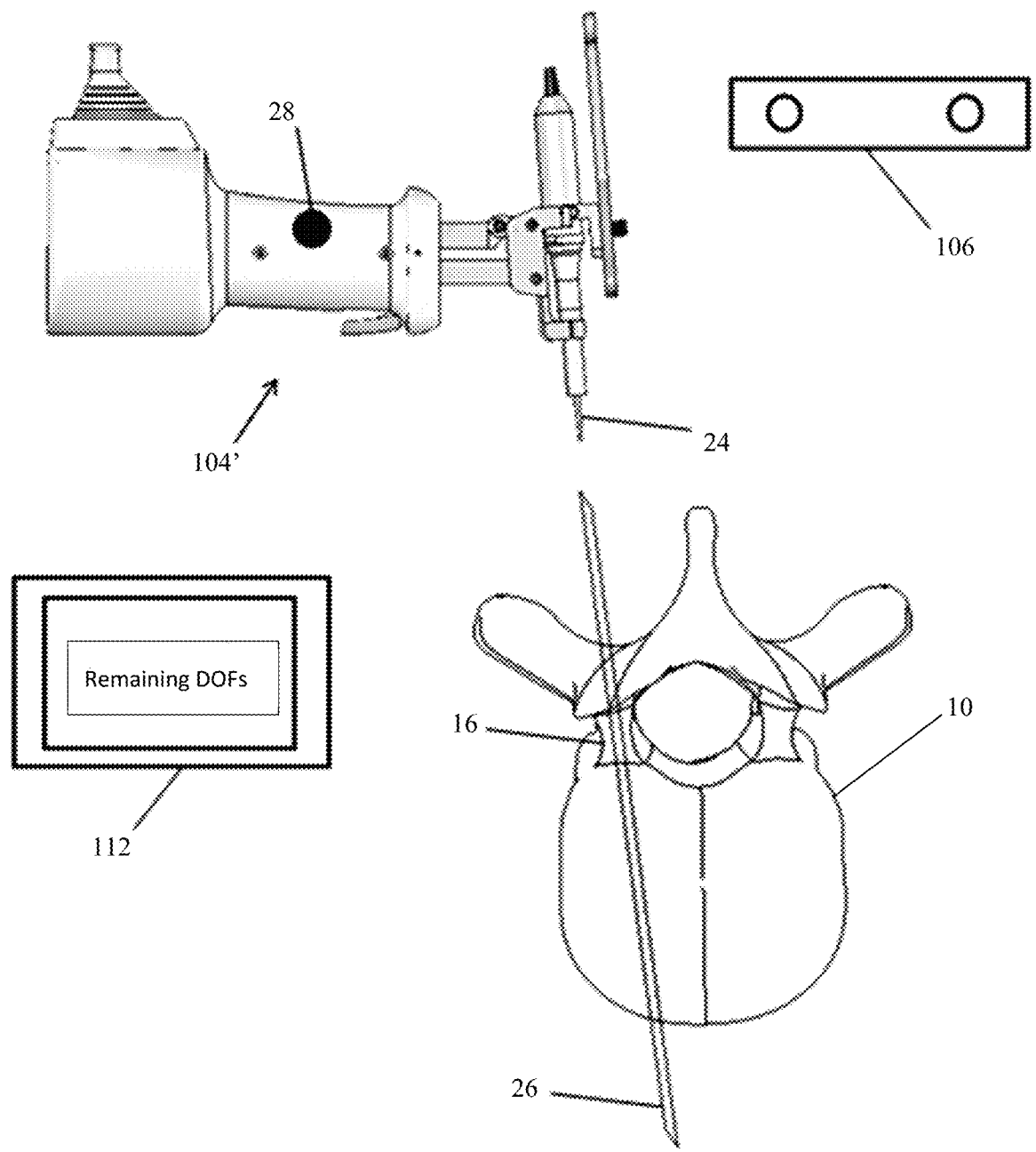
FIG. 5 illustrates the implantation of pedicle screws in a patient spinal column in accordance with embodiments of the invention.

The surgical plan is created, either pre-operatively or intra-operatively, by a user using planning software. The planning software may be used to a generate three-dimensional (3-D) models of the patient's bony anatomy from a computed tomography (CT), magnetic resonance imaging (MRI), x-ray, ultrasound image data set, or from a set of points collected on the bone intra-operatively. A set of 3-D computer aided design (CAD) models of the manufacturer's pedicle screws may be pre-loaded in the software to further assist the user to define the virtual pedicle screw plane to designate the best fit, position and/or orientation of the pedicle screw in the pedicle. For example, with reference to FIG. 5, a 3-D model of the patient's spinal column 10 is shown. The final placement of the pedicle screw 24 in the bone model of the spinal column 10 defines the pedicle planes 26 where the bone is drilled intra-operatively to receive the pedicle screw 24 as desired. Surgical device 104' is a 2-DOF device, which may include an on-board indicator 28 to indicate when a pin/screw 24 is aligned with the pedicle plane 26.

The surgical plan contains the 3-D model of the patient's operative bones (vertebrae) combined with the location of one or more virtual pedicle planes 26. The location of the pedicle virtual plane(s) 26 may be defined by the user in the planning software. In a particular embodiment, a user may locate three medial-lateral center points on the model of the pedicle to define a desired pedicle screw plane 26. In another embodiment, the user may virtually place a model of a pedicle screw in a desired POSE on the model of the pedicle. After which, the pedicle screw plane 26 may be defined by a longitudinal center axis of the pedicle screw and at least one non-collinear point translated from the center axis in the superior-inferior (SI) direction of the pedicle. It should be appreciated, that the final POSE of the model of the pedicle screw in the model of the pedicle provides the other relevant degrees of freedom such as the desired SI location, SI angle, and depth. In yet another embodiment, the planning system may include tools to outline a plane in a desired POSE on the pedicle 16. Ultimately, the location of the virtual plane(s) 26 is defined to aid in the placement of the pedicle screws 24 in the correct POSE. In another embodiment, if a robotic system having a robotic arm is used to execute the procedure, the trajectory to insert the pedicle screw with the robotic arm may be defined in the planning software as the position of a longitudinal center axis of the pedicle screw model relative to the bone model. Only the center axis is needed to define the trajectory relative to the bone.

In a particular embodiment, the user or the computing system 102 may activate the drill tool of the 2-DOF device when properly aligned with the pedicle plane 26 to drill pilot holes for the pedicle screws 24. The pedicle screws 24 are then drilled into the pilot holes using a standard drill. In another embodiment, the user may directly drill the pedicle screw 24 into the pedicle plane 26 without the need for a pilot hole with the drill tool of the 2-DOF device.

There are multiple advantages to using the 2-DOF surgical system 100 to accurately place the pedicle screws 24. For one, the surgical device 104 is actuating in real-time, therefore the user is actively guided to the POSE of the pedicle plane 26. In addition, the correct position and orientation of the pedicle screws 24 is accurately maintained regardless of the surgeon's placement of the hand-held portion 204 of the 2-DOF surgical system 100. Use of a hand-held actuator also avoids the possibility of inaccuracy in critical directions due to unintended mechanical deflection of a drill guide when a drill is guided through the guide, such as when a robot arm is used to simply hold a drill guide in place. In addition, traditional passive robotic arms and systems are unable to compensate for breathing or cardiac output even with inertia delayed compensatory mechanisms.

Figure 10:
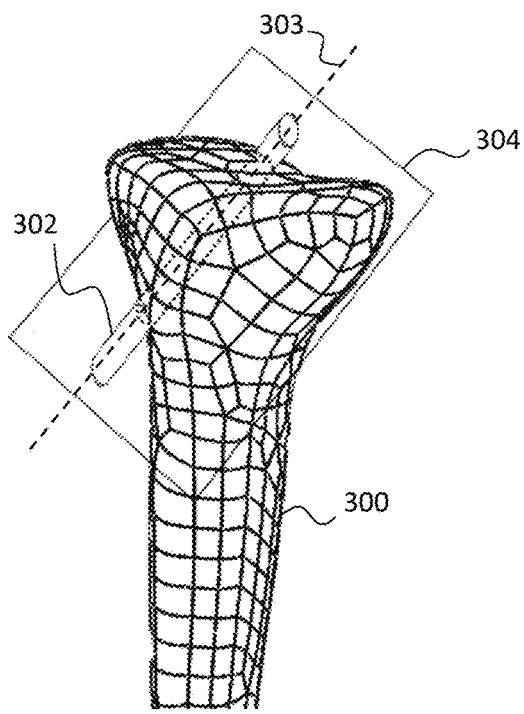
FIG. 10 depicts a 3-D tibial bone model with a planned position of a bone tunnel having an axis, and a virtual plane defined relative to the bone tunnel in accordance with embodiments of the invention.

In a specific inventive embodiment, the one or more indicators (223, 1906) on a 2-DOF device (104, 104') or feedback from a monitor 112 may be used in another inventive method to align the end-effector (e.g., pedicle screw, bone pin, drill bit) of the 2-DOF on a line (e.g., an axis, an optimal trajectory for a pedicle screw, a bone tunnel). In the inventive method to align a 2-DOF hand-held surgical device along an axis, a plane is defined relative to a desired location for an implant or tunnel on a bone, where the implant or tunnel has an axis. For example, FIG. 10 depicts a 3-D tibial bone model 300 with a planned position of a bone tunnel 302 having an axis 303, and a virtual plane 304 defined relative to the bone tunnel 302.

Figure 11:
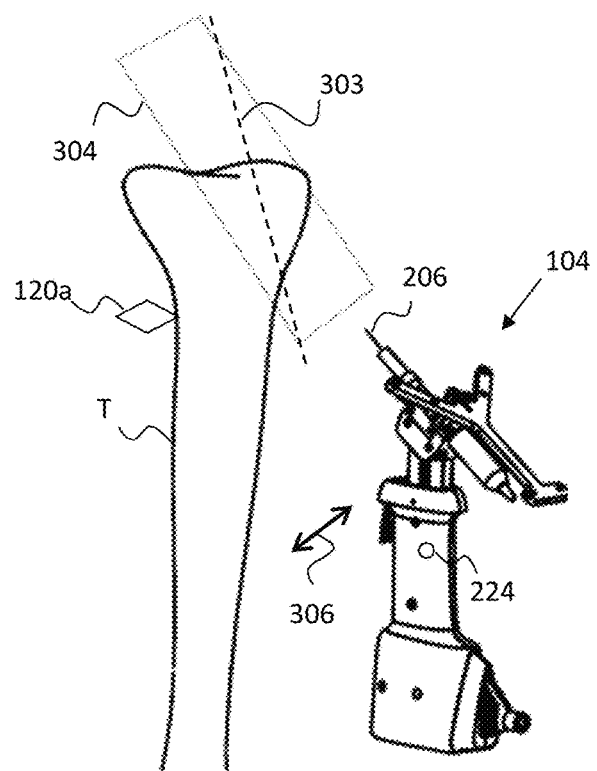
FIG. 11 depicts an end-effector of the two degree of freedom (2-DOF) surgical device aligned coincident with the defined plane, where the 2-DOF surgical device is moved side-to-side while the end-effector remains coincident with the defined plane by the actuation of the working portion in accordance with embodiments of the invention.

An end-effector of a 2-DOF surgical device is aligned coincident with the plane, and the 2-DOF surgical device is moved side-to-side while the end-effector maintains coincidence with the plane until a first indicator signals when the end-effector aligns with an entry point for the desired location for the implant or tunnel on the bone. FIG. 11 depicts an end-effector 206 of the 2-DOF surgical device 104 aligned coincident with the defined plane 304, where the 2-DoF surgical device 104 is moved side-to-side (as indicated by arrow 306) while the end-effector 206 remains coincident with the defined plane 304 by the actuation of the working portion 204.

Figure 12:
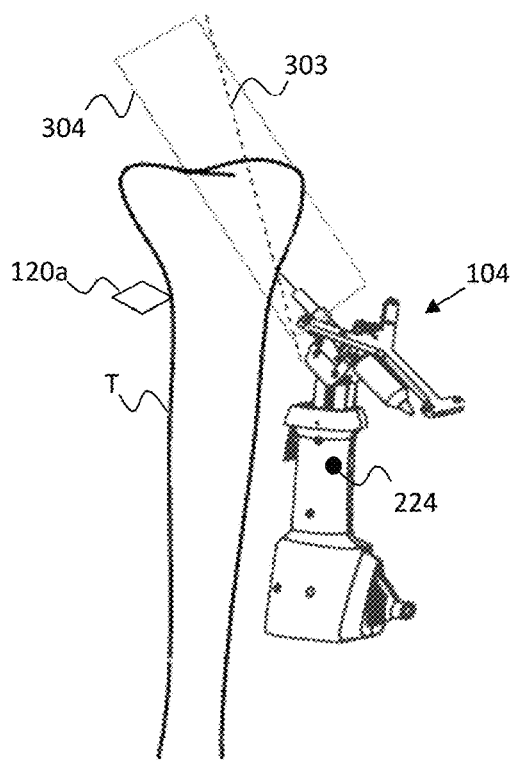
FIG. 12 depicts a tip of the end-effector anchored in the tibia at an entry point of the defined location for the implant or tunnel, where the tip is anchored after an indicator signals when the end-effector is aligned with the entry point in accordance with embodiments of the invention.
Figure 13:
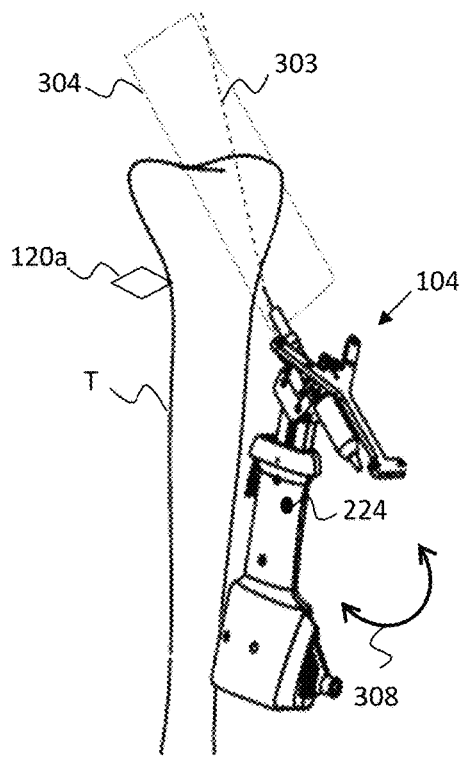
FIG. 13 depicts the 2-DOF surgical device being rotated about the anchored tip until the end-effector aligns with the defined location of the axis of the implant or tunnel, and a second indicator then signals to the user when the end-effector is aligned with the axis in accordance with embodiments of the invention.

Subsequently, a tip of the end-effector is anchored into the bone at the entry point; and the 2-DOF surgical device is rotated about the anchored tip while the end-effector remains coincident with the plane until a second indicator signals when the end-effector aligns with the axis of the implant or tunnel at the desired location. The end effector may then be inserted into the bone. FIG. 12 depicts a tip of the end-effector 206 anchored in the tibia T at an entry point of the defined location for the implant or tunnel, where the tip is anchored after an indicator 224 signals when the end-effector is aligned with the entry point. FIG. 13 depicts the 2-DoF surgical device 104 being rotated (as indicated by the arrow 308) about the anchored tip until the end-effector 206 aligns with the defined location of the axis 303 of the implant or tunnel. A second indicator then signals to the user when the end-effector is aligned with the axis 303.

After the end-effector is aligned with the axis 303, the end-effector is inserted into the bone. If the second indicator is power control, the drill (e.g., motor 205) automatically turns on when the end-effector 206 is aligned with the axis 303 and remains on while inserting the end-effector 206 into the bone. If at any point the end-effector 206 veers off-axis from the axis 303 while inserting the end-effector 206 in the bone, the drill (e.g., motor 205) is automatically turned off.

In specific inventive embodiments, the first indicator and second indication may be from the same indicator or different indicators. Preferably, the first indicator is an LED on the 2-DOF device that signals the entry point by way of a change in color or blinking frequency. Alternatively or in combination, the first indicator may be visual feedback displayed on a monitor. For example, a virtual model of the bone may be displayed on the monitor, where the defined plane, axis of the implant or tunnel, and the real-time axis of the end-effector are superimposed on the virtual bone model.

The user may then try and align the real-time superimposed axis of the end-effector with the superimposed axis of the implant or tunnel. Additional visual feedback on a monitor may include a simple red and green signal, a blinking light that changes frequency based on how closely it aligns with the entry point. However, keeping the indicator LED on the device makes it easier for the user to operate as they don't have to keep looking back and forth between the bone and the monitor. As for the second indicator, the same mechanisms may be used as the first indicator. But, preferably, the second indicator acts as a power control to the end-effector. For example, once the end-effector aligns with the axis of the implant or tunnel, the power to the drill is automatically turned on to insert the end-effector into the bone. If the user at any point veers off-axis from the axis (or the tip moves from the entry point), then power to the drill is automatically turned off.

In specific inventive embodiments, the end-effector may include a drill bit, pedicle screw, bone screw, bone pin, a hollow drill bit, burr, bone nail, a reamer, broach, or an implant. The end-effector does not necessarily have to drive in an implant (e.g., a pedicle screw, THA femoral stem). For example, the end-effector may be a drill bit that first drills a pilot hole for a pedicle screw, or, the end-effector may align a reamer along the central axis of an acetabular cup implant in THA to prepare the acetabulum.

In specific inventive embodiments, the plane may be defined in several different ways. Conventional methods may include using pre-operative bone data (CT, MRI, images, 3D bone models) and pre-operative planning software program. The desired placement for the implant or tunnel may be defined using various tools or widgets in the planning software program (e.g., virtual models of tunnels, virtual models of an implant, a set of points, lines, splines, or planes positionable relative to the pre-operative bone data, a drawing toolbox, etc). Once the position of the implant or tunnel is defined, the plane may be defined in several ways. For example, the plane may be defined using at least one of: the axis of the implant or tunnel and one additional point; or a central point (e.g., entry point) along the axis of the implant or tunnel and two additional points. The one or two additional points may be defined by the user on the pre-operative bone in the planning software or automatically assigned by the planning software. The user may define the one or two additional points on the pre-operative bone data (e.g., bone models) based on the expected exposure of the bone during the procedure. The one or two additional points may be anatomical landmarks defined by the user or the planning software. The planning software may further define the plane and/or the additional points using historical patient case data from previous surgeries. The location of the pre-operatively defined plane may be registered to the bone in the operating room using registration techniques known in the art.

Alternatively or in combination in specific inventive embodiments, the plane may be defined on the exposed bone. For example, a user may digitize three points on the bone with a tracked digitizer or the tracked 2-DOF surgical device to define a plane, or the plane may be defined using an axis and one additional point. The axis may be defined by aligning the axis of the digitizer or end-effector of the device on the bone, where the axis of the digitizer or end-effector is recorded by the computing system to define an axis on the bone. The one additional point is then defined by digitizing a point on the bone with a digitizer or 2-DOF surgical device.

Articulating Screw-Driving Device

The articulating device 204 of the 2-DOF surgical system 100 described above can accurately align a tool/pin/screw to be coincident with one or more virtual planes. However, the surgeon still has to manually advance the device 204 towards the bone to insert the screw or to create a pilot hole for the screw, which may be uncomfortable for the surgeon. In other words, the 2-DOF device is only capable of aligning a tool/pin/screw in the screw plane 26, while the user has to manually control the depth (anterior-posterior direction) of the pin/screw. If an active robotic arm is used however, the robotic arm may control all degrees of freedom to insert a pedicle screw including depth.

Figure 6A:
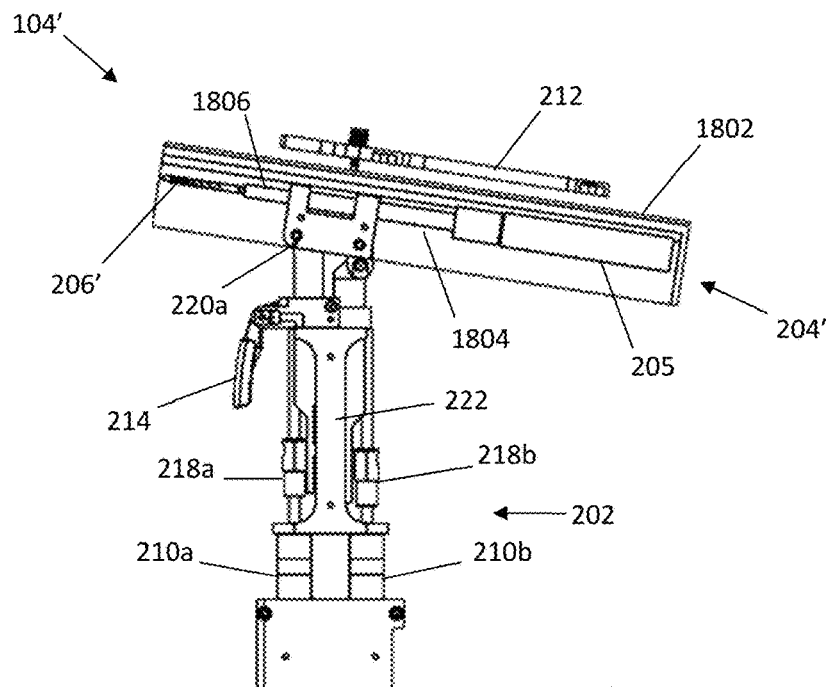
FIGS. 6A and 6B depict a cross-section of an articulating pin/screw-driver device, where
Figure 6B:
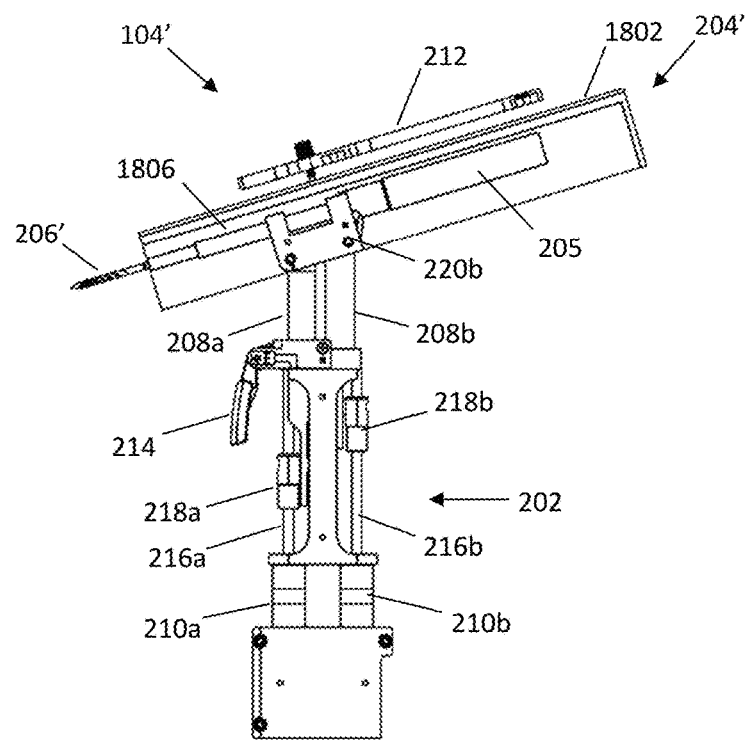
Figure 6C:
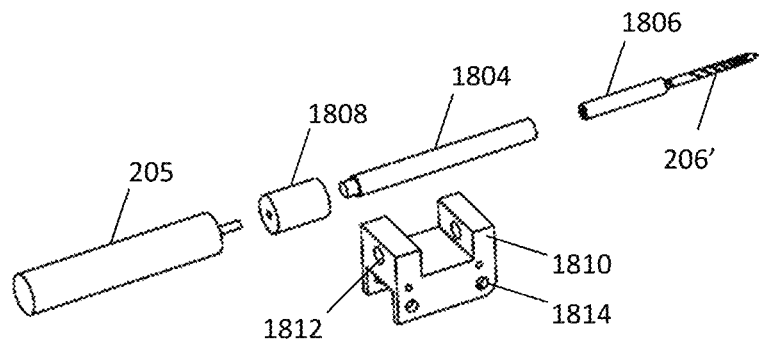
FIG. 6C is an exploded view that illustrates the components of a working portion of the pin/screw-driver device in accordance with embodiments of the invention.

To provide further control and feedback for the user with the 2-DOF surgical device 104, the 2-DOF surgical device 104 may be modified to include a third pin/screw-driving degree-of-freedom, which will be referred to hereinafter as an articulating pin/screw-driver device 104'. With reference to FIGS. 6A-6C in which like reference numerals have the meaning ascribed to that numeral with respect to the aforementioned figures, a particular embodiment of the articulating pin driver device 104' is shown. In addition to the components of the 2-DOF surgical device 104, the working portion 204' of the articulating pin driver device 104' further includes components configured to drive a pin 206' into a bone. Specifically, with reference to FIG. 6C, the working portion 204' includes the motor 205, a motor coupler 1808, a pin-driving ball screw 1804, a pin holder 1806, and the pin 206'. A specially adapted carriage 1810 is configured to support and carry the working portion 204' and may include mechanisms for actuating the pin. In some inventive embodiments, the carriage 1810 includes a pin-driving ball nut 1812 and connection members 1814 such as holes, bearings, or axle supports to receive a rod, a dowel, or an axel to act as the hinges (220a, 220b) that are connected with the first end of the linear rails (208a, 208b). The motor coupler 1808 couples the motor 205 with the pin-driving ball screw 1804. The pin-driving ball screw 1804 is in mechanical communication with the pin-driving ball nut 1812. The pin holder 1806 connects the pin-driving ball screw 1804 with the pin 206'. The pin 206' is removably attached with the pin holder 1806 to allow the pin 206' to remain in the bone when inserted therein. The motor 205 may bi-rotationally drive the pin-driving ball screw 1804 and the pin 206' to advance and drive the pin 206' into a bone. The components may further include a motor carriage (not shown) operably connected with a motor linear rail (not shown). The motor carriage is secured to the motor 205 to keep the motor 205 from rotating while allowing the motor 205 to translate along the motor linear rail. The motor linear rail may extend from the carriage 1810. FIG. 6A illustrates the pin/screw 206' in a retracted state and FIG. 6B illustrates the pin/screw 206' in an extended state, where the pin 206' can translate a distance "d2". An outer guard 1802 may be present to guard the user from the actuating mechanisms in the working portion 204'. If an outer guard 1802 is present, the guard 1802 may be dimensioned to conceal the entire pin 206' when the pin 206' is in the retracted state, or the guard 1802 may only conceal a portion of the pin 206' to allow the user to visualize the tip of the pin 206' prior to bone insertion.

In a specific embodiment, the working portion 204' may include a first motor 205 for rotating the pin 206', and a second motor (not shown) for translationally driving the pin 206'. The second motor may rotate a ball screw or a worm gear that is in communication with an opposing ball nut or gear rack configured with the first motor 205. As the second motor bi-rotationally drives the ball screw or worm gear, the first motor 205 and the pin 206' translate accordingly.

The device computer 108 of the articulating pin driving device 104' may further include hardware and software to control the pin-driving action. In an embodiment, the device computer 108 includes two motor controllers for independently controlling the front actuator 210a and back actuator 210b, respectively, to maintain the POSE of the working portion (204, 204'). A third motor controller may independently control the motor 205 for driving and rotating the pin 206' into the bone. In the specific embodiment where a first motor 205 rotates the pin 206' and a second motor (not shown) translates the pin 206', the device computer 108 may include two separate motor controllers to independently control the first motor 205 and the second motor.

Figure 7A:
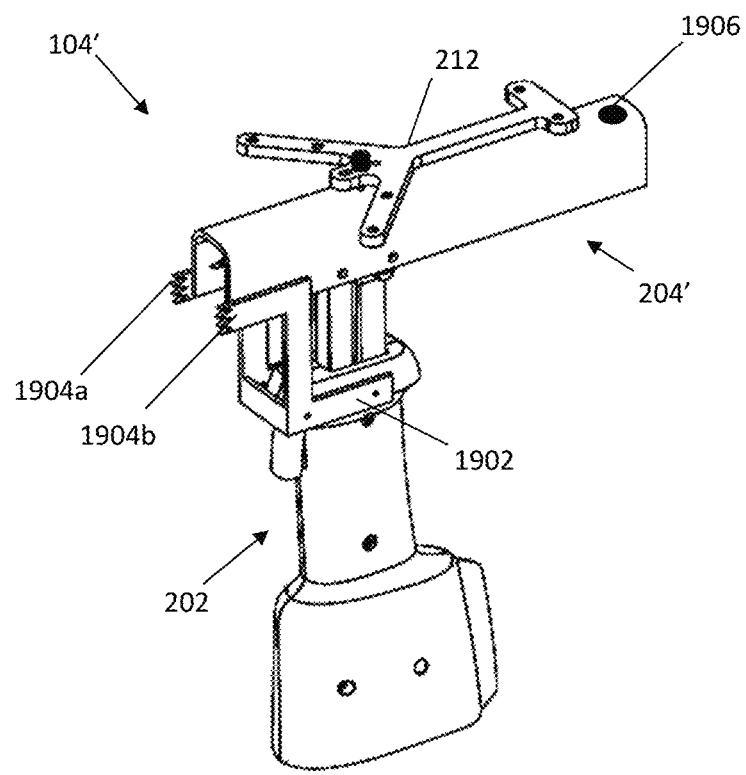
FIGS. 7A and 7B depict and illustrate a bone stability member attached to the pin-driver device and the use thereof in accordance with embodiments of the invention.
Figure 7B:
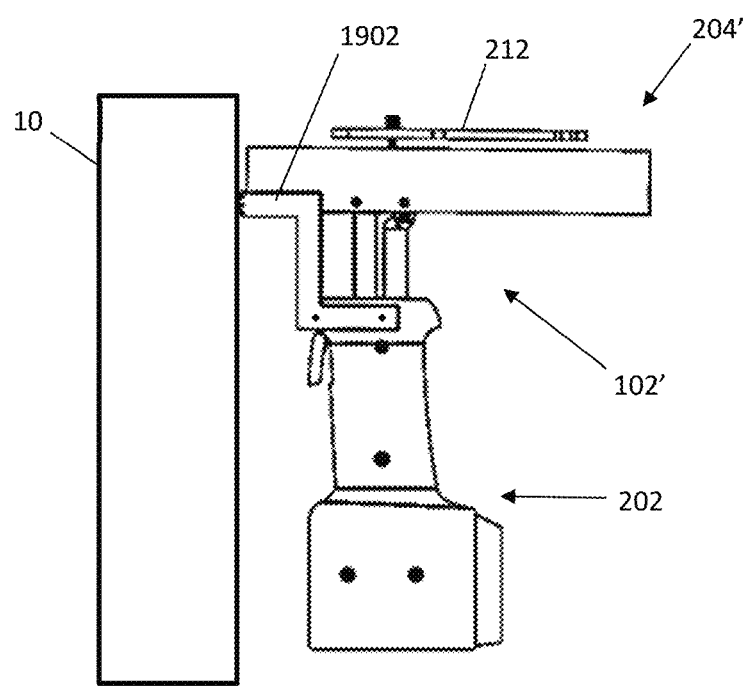

In a specific embodiment, with reference to FIGS. 7A-7B, the articulating device 104' includes a bone stabilizing member 1902 attached or integrated with the hand-held portion 202. The bone stabilizing member 1902 includes one or more contacting elements (1904a, 1904b) which are configured to contact the bone and/or skin surface to stabilize the hand-held portion 202 while the working portion 204' articulates. The contacting elements (1904a, 1904b)

may be a flat surface, a pointed protrusion, or a surface having jagged edges to interact with the bone and/or soft tissue and stabilize the hand-held portion 202. The one or more contacting element(s) (1904a, 1904b) may project just beyond the working portion 204' such that the element(s) (1904a, 1904b) may contact the bone without negatively impacting how deep the pin/screw 206' may be inserted in the bone. Alternatively, the contacting elements (1904a, 1904b) may project laterally (i.e., perpendicular to the pin axis) from the hand-held portion such that the contacting elements (1904a, 1904b) interact with the skin surface of the patient. When the user is in the approximate region for driving the pin/screw 206', the user may stabilize the hand-held portion 202 to the bone and/or soft tissue via the contacting elements (1904a, 1904b). With the hand-held portion stabilized, the working portion 204' further articulates until the pin/screw 206' is precisely coincident with a virtual pin plane. In a specific embodiment, once the pin/screw 206' aligns with the virtual pin plane 214, the system 100 automatically locks the actuators (210a, 210b) and activates the motor 205 to drive the pin/screw 206' into the bone. In another embodiment, the user activates a user input mechanism such as a trigger 214 or a button before the system 100 either locks the actuators (210a, 210b), drives the pin/screw 206', or both. Therefore, the user can anticipate and control when the pin/screw 206' is driven into the bone. This user input mechanism may similarly be used by the user to control the amount of extension or retraction of the pin/screw 206' in general.

In a particular inventive embodiment, with reference to FIG. 7A, one or more indicators 1906, such as an LED or a display, is attached or integrated with the device 104'. The indicator 1906 may be attached to the outer guard 1802, the working portion 204', or the hand-held portion 202 for example. The indicator(s) 1906 provide feedback to the user as to a current position of the device 104' with respect to a desired position for the device 104'. For example, the indicator 1906 may emit a red light to indicate that the device 104' is outside of the travel ranges of the three ball screws (216a, 216b, 1804). In other words, a red light is emitted when the working portion 204' and pin/screw 206' can no longer be articulated to reach a desired position, orientation, or a desired depth to insert the pin/screw 206'. The indicator 1906 may emit a yellow light when the user is approaching the travel ranges and a green light when the pin/screw 206' is aligned with a virtual pin plane. The indicator 1906 may further produce a blinking light that changes in blinking frequency based on how close the device 104' is to exceeding the travel range, or how close the pin/screw 206' is to a virtual pin plane. The indicator 1906 may also indicate when the device 104' is ready to autonomously place the pin inside the bone. In a particular embodiment, the working portion 204' does not actuate until the indicator 1906 is in an active state, where the active state is triggered when the device 104' is within the travel limits of the ball screw. This data conveyed by the indicator 1906 is readily available based on either: a) local data collected directly from the device 104', such as the device kinematics; b) the tracking data collected from the tracking system 106; c) a comparison of the POSE of the device 104' with the surgical plan; or d) a combination thereof.

Figure 8A:
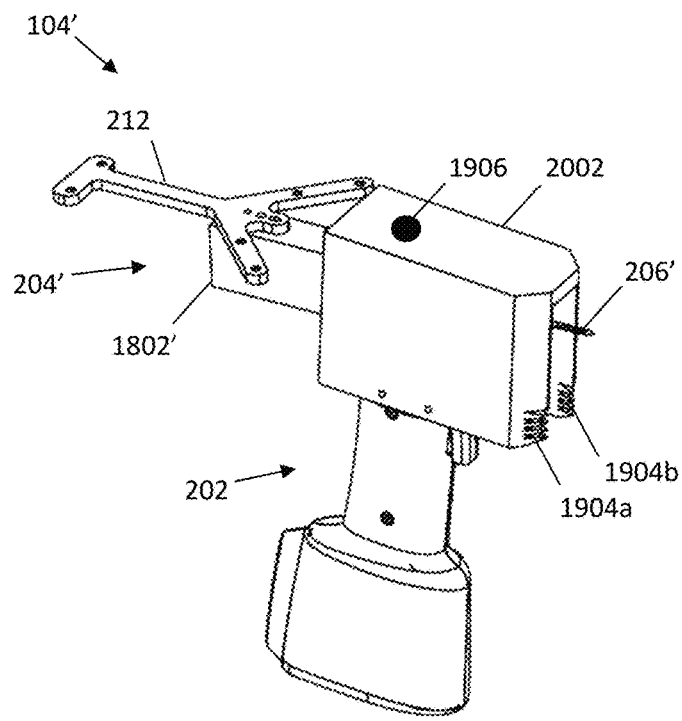
FIGS. 8A and 8B depict a partial enclosure enclosing the working portion in accordance with embodiments of the invention.
Figure 8B:
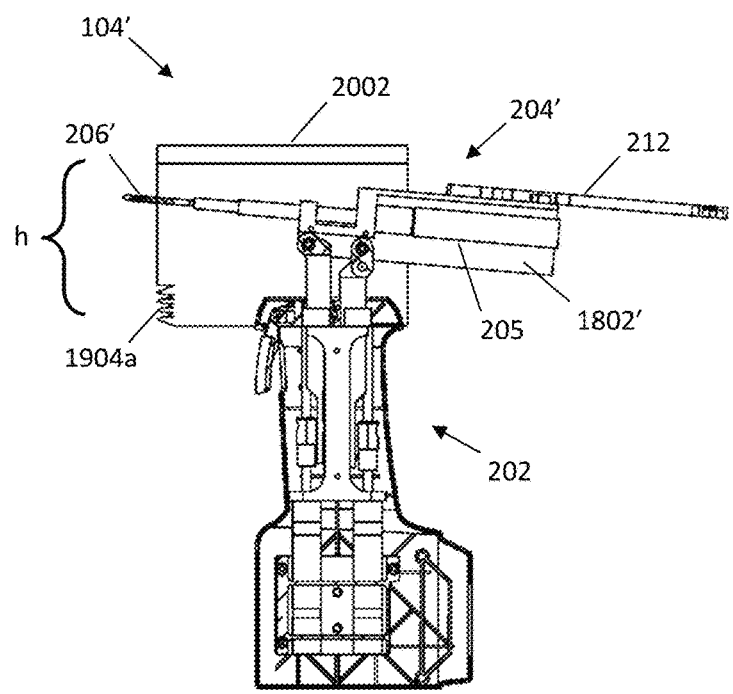

In a specific inventive embodiment, with reference to FIGS. 8A and 8B, the articulating device 104' includes a partial enclosure 2002. FIG. 8A is perspective view of the articulating device 104' with the partial enclosure 2002 and FIG. 8B is a cross-section view thereof. The partial enclosure 2002 is attached to the hand-held portion 202 and partially encloses the working portion 204'. The working portion 204' is able to articulate within the partial enclosure 2002. The partial enclosure 2002 has an internal dimension (i.e. height or diameter) of 'h' that corresponds to the travel range of the working portion 204'. This dimension 'h' may account for the translation 'd' of the working portion 204' and any additional height required to account for the pitch 'a' of the working portion 204'. The advantage of the partial enclosure 2002 is to provide the user with a guide as to the workspace or travel range of the working portion 204'. The user can simply place a front end of the partial enclosure 2002 on the bone to stabilize the hand-held portion 202, at which time the working portion 204' can articulate to a virtual pin plane and drive the pin/screw 206' into the bone. The user is no longer trying to aim the small pin/screw 206' directly to a pin/screw plane, but is rather using a larger guide, the partial enclosure 2002, to get the pin/screw 206' in the general vicinity of a pin/screw plane and allowing the working portion 204' to perform the alignment. In addition, the user no longer has to worry about exceeding the travel limits of the working portion 204' while aligning the pin/screw 206'.

The front end of the partial enclosure 2002 may act as a bone contacting element (1904a, 1904b) to stabilize the hand-held portion 202 and may further include features such as a jagged edge or one or more pointed protrusions.

The pin/screw 206' extends beyond the partial enclosure 2002 in the extended state to allow the pin to be driven into the bone as shown in FIG. 8B. When the pin/screw 206' is in the retracted state, the pin/screw 206' is enclosed within the partial enclosure 2002.

The partial enclosure 2002 may further include the indicator 1906 to aid the user in positioning the device 104' to a desired pin plane as described above.

The partial enclosure 2002 is further configured to allow the tracking array 212 to attach with the working portion 204', or an outer guard 1802' of the working portion 204', to permit the tracking system 106 to track the POSE of the working portion 204' as it articulates.

Figure 9A:
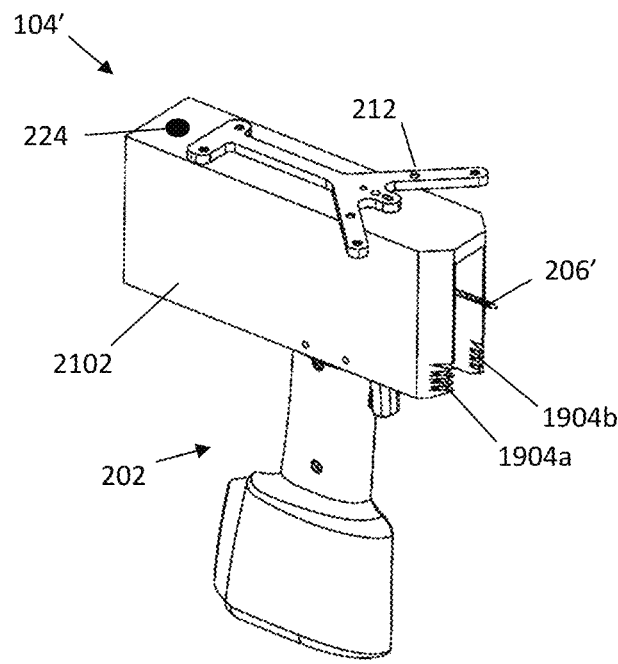
FIGS. 9A and 9B depict a full enclosure enclosing the working portion in accordance with embodiments of the invention
Figure 9B:
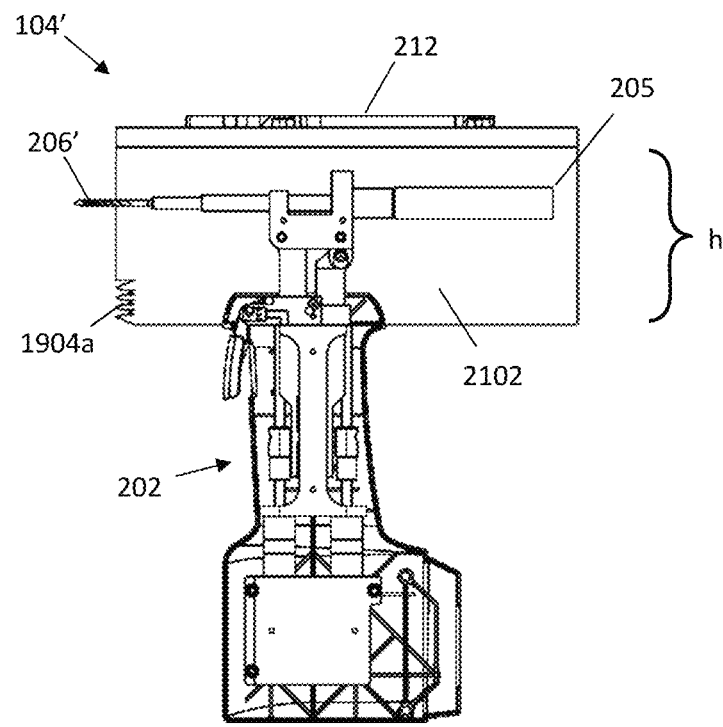

In a particular inventive embodiment, with reference to FIGS. 9A and 9B, the articulating device 104' includes a full enclosure 2102. FIG. 9A is a perspective view of the articulating device 102 with the full enclosure 2102 and FIG. 9B is a cross-section view thereof. The full enclosure 2102 is configured with the same principles and has the same advantages as the partial enclosure 2002, except the tracking array 212 is attached directly to the full enclosure 2102. Since the tracking array 212 is attached to the full enclosure 2102, the control scheme for controlling the working portion 204' must be modified, where the device kinematics are used to determine the POSE of the working portion 204'. Particularly, the tracking system 106 tracks the hand-held portion 202 based on the geometric relationship between the array 212 and the hand-held portion 202, and the actuator (210a, 210b) positions (i.e. the rotational position of the actuators that corresponds to the position of the ball nuts (218a, 218b) on the ball screws (216a, 216b)) are used to determine the POSE of the working portion 204' with respect to the hand-held portion 202. Therefore, the computing system 102 can determine new actuator positions to control and align the pin/screw 206' with a virtual pin plane.

It should be appreciated that the partial enclosure 2002 and full enclosure 2102 may be sized and adapted for assembly to a hand-held system having greater than two degrees of freedom with similar advantages. For example, it is contemplated that the inner dimensions of the enclosure (226, 228) may accommodate the travel limits of a device having an articulating portion that articulates in one or more translational directions, pitch, and yaw such as the system described in U.S. Patent Publication No. 2013/0060278. However, as the number of degrees of freedom increase, so does the size of the enclosure (226, 228) which may impede the operating workspace.

It should be further appreciated that the embodiments of the bone stabilizing member 1902, the indicator 1906, the partial enclosure 2002, and full enclosure 2102, can all be adapted for use with the 2-DOF surgical device 104 as shown in FIGS. 4A-4B.

Bi-Cortical Drilling

To further stabilize the pedicle screws in the bone it may be desirable to drill the pins through two cortical regions of the bone, also referred to as bi-cortical drilling. However, if a drill bit or a pedicle screw is drilled beyond the second cortical region and into the soft tissue, patient harm can occur. Therefore, it is proposed that the third pin-driving actuation axis can also be used to retract the drill bit/pin if the drill bit/screw breaks through the second cortical region.

In a particular inventive embodiment, bone breakthrough is detected using an existing method, such as the method described in Taha, Zahari, A. Salah, and J. Lee. "Bone breakthrough detection for orthopedic robot-assisted surgery." *APIEMS* 2008 *Proceedings of the 9th Asia Pacific Industrial Engineering and Management Systems Conference*. 2008. The articulating pin-driving device 104' then automatically retracts the drill bit/pin at a constant optimal retraction speed relative to the bone, regardless of how the user is moving the hand-held portion 202. This ensures that if the drill bit/pin breakthrough the second cortical region, that the drill bit/pin is retracted so as to not cause any patient harm. The retraction speed is a function of the optimal retraction speed combined with the current speed of the hand-held portion 202.

The relative speed between the hand-held portion 202 and the bone can be measured several different ways. In one embodiment, the speed of the hand-held portion 202 relative to the bone is not detected and instead a speed is assumed. In another embodiment, a simple linear distance measuring tool is used, such as a laser distance measurement device. In a particular embodiment, the tracking system 106 is used to track both the bone and the hand-held portion 202 using one or more fiducial markers on each of the bone and the hand-held portion 202.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes can be made in the function and arrangements of elements without departing from the scope as set forth in the appended claims and the legal equivalents thereof.

Patents, patent application publications, and other literature references cited herein are indicative of the level of the skill in the art. Each patents, patent application publication, and other literature reference is hereby incorporated by reference, each in its entirety. These references are intended to be incorporated to the same extent as is each reference was individual incorporated by reference.

The foregoing description is illustrative of particular embodiments of the invention, but is not meant to be a limitation upon the practice thereof. The following claims, including all equivalents thereof, are intended to define the scope of the invention.

The invention claimed is:

1. A method to align a 2-DOF hand-held surgical device along an axis, comprising:
    defining a plane relative to a desired location for an implant or tunnel on a bone, said implant or tunnel having an axis;
    aligning an end-effector of the 2-DOF surgical device coincident with the plane;
    moving the 2-DOF surgical device about the bone while the end-effector maintains coincidence with the plane until a first indicator signals when the end-effector aligns with at least one of: an entry point for the desired location for the implant or tunnel on the bone; or the axis of the implant or tunnel at the desired location; and
    moving the 2-DOF surgical device side-to-side while the end-effector maintains coincidence with the plane until the first indicator signals when the end-effector aligns with the entry point for the desired location for the implant or tunnel on the bone;
    anchoring a tip of the end-effector into the bone at the entry point; and
    rotating the 2-DOF surgical device about the anchored tip while the end-effector remains coincident with the plane until a second indicator signals when the end-effector aligns with the axis of the implant or tunnel at the desired location.

2. The method of claim 1 further comprising inserting the end-effector into the bone.

3. The method of claim 1 wherein the first indicator and the second indicator are the same indicator.

4. The method of claim 1 wherein the first indicator is at least one of: a red and a green signal; and a blinking light that changes frequency based on how closely the end-effector aligns with the entry point or axis of the implant or tunnel at the desired location.

5. The method of claim 1 wherein the second indicator is at least one of: a red and a green signal; and a blinking light that changes frequency based on how closely the end-effector aligns with the axis of the implant or tunnel at the desired location.

6. The method of claim 1 wherein the first indicator is displayed using a monitor, or an on-board indicator of the 2-DOF surgical tool that provides feedback to the user.

7. The method of claim 6 wherein the first indicator is displayed on the on-board indicator of the 2-DOF surgical tool and the on-board indicator of the 2-DOF surgical tool comprises one or more light emitting diode (LED) for direct visual feedback when the 2-DOF surgical tool is aligned with at least one of the entry point or the axis of the implant or tunnel.

8. The method of claim 7 further comprising displaying a virtual model of the bone is on the monitor, where the defined plane, axis of the implant or tunnel, and a real-time axis of the end-effector are superimposed on the virtual model of the bone.

9. The method of claim 8 further comprising aligning the real-time axis of the end-effector with the axis of the implant or tunnel.

10. The method of claim 7 wherein the monitor further provides visual feedback as at least one of: a red and a green signal; and a blinking light that changes frequency based on how closely the end-effectors aligns with the entry point.

11. The method of claim 1 wherein the second indicator is a power control to the end-effector wherein when the end-effector aligns with the axis of the implant or tunnel, the power to a drill of the end-effector is automatically turned on to insert the end-effector into the bone; and
wherein if the end-effector veers off-axis from the axis, or the tip moves from the entry point, then power to the drill is automatically turned off.

12. The method of claim 1 wherein the end-effector comprises one of a dill bit, pedicle screw, bone screw, bone pin, a hollow drill bit, burr, bone nail, a reamer, broach, or an implant.

13. The method of claim 1 wherein the plane is defined using pre-operative bone data (CT, MRI, images, 3D bone models) and a pre-operative planning software program.

14. The method of claim 1 wherein the desired placement for the implant or tunnel is defined using tools or widgets in a planning software program, the tool and widgets comprising at least one of virtual models of tunnels, virtual models of an implant, a set of points, lines, splines, or planes positionable relative to a set of pre-operative bone data, and a drawing toolbox.

15. A system for implementing the method claim 1 wherein said system comprises:
a computing system;
an articulating 2-DOF surgical device, wherein the articulating 2-DOF surgical device comprises:
a hand-held portion;
a working portion movably coupled to the hand-held portion by a front linear rail and a rear linear rail, said front linear rail and said rear linear rail actuated by a set of components in the hand-held portion to adjust pitch and translation of the working portion relative to the hand-held portion; and
a tracking array comprising a set of three or more fiducial markers coupled to the working portion to permit a tracking system to track a position and orientation (POSE) of the working portion; and
a tracking system.

16. The system of claim 15 further comprising:
a front actuator that powers a front ball screw, and a back actuator that powers a back ball screw, where the first end of both said front linear rail and said rear linear rail are each attached to said working portion via a set of hinges allowing said working portion to pivot relative to said front linear rail and said rear linear rail; and
a set of ball nuts integrally attached at a second end of both said front linear rail and said rear linear rail, said set of ball nuts in mechanical communication with both said front ball screw and said back ball screw; said set of ball nuts translate along the axis of the ball screws to adjust the pitch and translation of said working portion.

17. The system of claim 15 wherein the articulating 2-DOF surgical device further comprises an on-board indicator configured to provide feedback to a user based on an actual position of said working portion relative to a desired position for said working portion.

* * * * *